United States Patent [19]

Cohen et al.

[11] Patent Number: 5,296,599
[45] Date of Patent: Mar. 22, 1994

[54] ACTIVATED CARBAMATES COMPOUNDS

[75] Inventors: Steven A. Cohen, Hopkinton; Dennis P. Michaud, Dracut, both of Mass.

[73] Assignee: Millipore Corporation, Bedford, Mass.

[21] Appl. No.: 762,579

[22] Filed: Sep. 19, 1991

[51] Int. Cl.$^5$ .................. C07D 237/20; C07D 215/38; C07D 217/26

[52] U.S. Cl. .................................. 544/235; 544/237; 546/104; 546/143; 546/159; 546/171; 548/407; 548/525

[58] Field of Search ............... 546/171, 159, 143, 104; 544/235, 237, 525; 548/407

[56] References Cited

PUBLICATIONS

Sosnovsky, et al., "Chemical Abstracts", vol. 115, No. 17, (1991) col. 115:183727c.

Shimada, et al., "Chemical Abstracts", vol. 111, No. 1, (1989) col. 111:3485h.
Nimura, N. et al., *Anal. Chem.* 58:2372–2375 (1986).
Takeda et al., *Tetrahedron Letter* 24:4569–4572 (1983).
Brynes, P. J. et al., *Analt. Biochem.* 116:408–413 (1981).

*Primary Examiner*—C. Warren Ivy
*Assistant Examiner*—James H. Turnipseed
*Attorney, Agent, or Firm*—Hamilton, Brook, Smith & Reynolds

[57] ABSTRACT

A class of novel heterocyclic aromatic carbamate compounds is described. A method of derivatizing amine-functional compounds with the novel carbamates is also disclosed. The derivatives can be detected using a fluorescence detector. The present composition and method allow femtomole quantities of amine compounds to be detected and measured.

4 Claims, 3 Drawing Sheets

ACTIVATED CARBAMATES COMPOUNDS

BACKGROUND OF THE INVENTION

There is considerable interest by biochemists, clinical chemists and pharmaceutical manufacturers in determining the concentration of amino acids, peptides and other amine-functional compounds in a complex biological sample. This analysis may require, for example, the determination of twenty or more amino acids at the picomole level. A typical application is the qualitative and quantitive analysis of the amino acids that are present in a synthetic peptide, perhaps one which has been synthesized by recombinant DNA methods. In this application, it is not uncommon for the analyst to be forced to work with sub-microgram quantities of a sample. Similarly, the analysis for amino acids in the blood of neonates, for example, demands the handling of very small samples.

In order to reduce the sample size to accomodate the potential scarcity of sample available and provide detection capability in the presence of non-amino acid components, the analytical method that is selected must provide a very high degree of sensitivity and detection selectivity. The sensitivity and selectivity of an assay for a compound is dependent on the instrumental response that it provides. Typical detection schemes involve the absorbance or emission of light, or the electrochemical reactivity of the compound(s) of interest.

The qualitative and quantitative analysis of complex mixtures of amino acids and/or peptides involves analyzing samples that may contain twenty or more amino acids, and in which the structural differences between many of the amino acids are subtle, e.g., the difference between leucine and valine is one methylene group in the aliphatic side chain. Thus, a high degree of selectivity is needed to distinguish them. A typical mixture contains amino acids with acidic, basic and neutral side groups.

The absorbance, fluorescence and electrochemical response of most amino acids is quite weak. A commonly used tactic to maximize the sensitivity of an assay is to convert the compound(s) of interest into a derivative that exhibits a better response than the compound of interest itself. The selection of a derivatizing agent is a critical choice in the development of an analytical procedure. The derivatizing agent affects the ultimate sensitivity and accuracy of the analysis by maximizing the sensitivity, yield and stability of the derivatized amino acids.

There are several criteria important for the utility of an derivatization method. The analytical procedure must provide accurate quantitation for each component present in a complex mixture. To accomplish this, it is necessary to resolve the components of interest, not only from each other, but from components generated by the derivatization procedure. Quantitative conversion of all underivatized amino acids, including secondary amino acids, to single products is highly desirable, and facilitates good quantitation.

Detection selectivity is another advantageous feature for amino acid derivatives. Underivatized amino acids all absorb weakly in the low UV (200-220 nm) range, but detection at such wavelengths is subject to interference by many compounds present in sample mixtures or chromatographic mobile phases. Derivatization with reagents absorbing at approximately 254 nm provides a measure of selectivity, but any aromatic organic compounds, frequently present in biological samples, can interfere at this wavelength. Reagents that enable detection via fluorescence, electrochemical response or visible-range absorbance would be desirable for superior detection selectivity.

Finally, it is necessary for derivatives to be sufficiently stable to allow separation and detection without significant degradation. Highly stable derivatives are also favorable as they allow a sample to be reanalyzed, if so desired, without assaying another sample.

In the past, a number of derivatization procedures have been developed to permit the assay of amino acids by high performance liquid chromatographic and electrophoretic separations. Four such procedures commonly utilized for this purpose include:

1) The o-phthalaldehyde (OPA)/mercaptan method. The OPA procedure can detect amino acids with a typical detectable level in the order of about 100 femtomole (fmol). The formation of the derivatives is rapid. A significant difficulty with this method is that the adduct is fairly unstable, and must be prepared very shortly before the detection step. An additional problem is that this reagent will not form a derivative with secondary amino acids.

2) The 9-fluorenylmethylchloroformate (FMOC method). The FMOC procedure provides for stable derivatives, with a minimum detectable level in the order of a few hundred fmol. There are a number of disadvantages with the FMOC procedure. Free tryptophan and cystine cannot be quantitated easily. The derivatizing reagent must be removed from the reaction mixture by an extraction step because it is itself fluorescent. The reagent has also been reported to form multiple derivatives with histidine. The reagent is also hazardous to work with, because it is corrosive and is a lachrymator.

3) The phenylisothiocyanate method (PITC). The PITC procedure yields stable derivatives which are formed rapidly. It can be used for both primary and secondary amino acids, as well as cystine. The method uses absorbance as the detection procedure, and can provide a minimum detection limit of 1 pmol. However, the derivatives are not fluorescent and detection must be performed at 254 nm, which does not allow for good detection selectivity.

4) The dansyl chloride method. The dansyl chloride method provides stable derivatives with a minimum detectability in the order of about 1.5 pmol. It is able to detect secondary amines and cystine, but it results in multiple derivatives.

In addition to the above methods, fluorescent succinimidocarbamates have been used as derivatizing agents for amines, amino acids, peptides, phosphates and other classes of compounds. When the succinimidocarbamate reagent is used to tag a compound with a fluorescent group, a detection limit of about 1 pmol can be achieved. These reagents are used in conjunction with modern separation techniques such as high performance liquid chromatography, thin layer chromatography or capillary electrophoresis. Nimura et al., *Anal. Chem.*, 58:2372-2375 (1986). Succinimidyl activated carbamates have been prepared by reacting carbocyclic aromatic amines with di-(N-succinimidyl) carbonate. Takeda et al., *Tetrahedron Lett.*, 24:4569-4572 (1983).

Improved methods for detecting and accurately measuring the presence and amount of amino-functional compounds, particularly amino acids and proteins, are needed. A method which allows detection of these compounds in subpicomole quantities in very small samples and which minimizes the amount of sample that is consumed in the analysis, is needed.

SUMMARY OF THE INVENTION

The invention relates to a class of heterocyclic aromatic carbamate compounds, and their use to detect small quantities of amine-functional compounds. The present carbamate compounds have the following general formula:

wherein ArNH represents a heterocyclic aromatic amine. The heterocyclic moiety can be any aromatic ring structure (e.g., up to about 25 carbon atoms in the ring), including polycyclic ring structures (e.g., up to about 5 rings), containing from about 1 to about 4 heteroatoms in the ring structure, such as nitrogen (N), oxygen (O), sulfur (S) and combinations thereof. One or multiple heteroatoms can be present outside the ring structure and include N, O, S, halogens (e.g., fluorine, chlorine, bromine) and combinations thereof. The heterocyclic moiety can be substituted with one or more non-reactive electron donating groups, such as alkyl groups (e.g., C1-C6 alkyl such as methyl or ethyl), alkoxy groups (e.g., C1-C6 alkoxy such as methoxy or ethoxy groups) or aromatic groups (e.g., phenyl groups). Heterocyclic aromatic amines which are useful to form the present carbamate compounds include, for example, aminoquinoline, substituted aminoquinoline, aminoisoquinoline, aminocoumarin, substituted aminocoumarin, aminoacridine or substituted aminoacridine.

A method for preparing the present heterocyclic aromatic carbamates is also the subject of the present invention. The method generally involves reacting the heterocyclic aromatic amine with di-[N-succinimidyl] carbonate under conditions appropriate to form the heterocyclic aromatic carbamate compound.

The present heterocyclic aromatic carbamate compounds are useful for derivatizing amine-functional molecules in order to tag them with a fluorescent group. The heterocyclic aromatic moiety is naturally fluorescent and can be used to derivatize and detect an amine-functional compound, the resulting derivative being fluorescent and readily detected at trace levels due to the high fluorescence quantum yield of the heterocyclic aromatic moiety. The method is particularly useful for detecting and measuring very small quantities, e.g., in the femtomole range, of amino acids, peptides, other amine-functional compounds, or aminated carbohydrates, including complex carbohydrates.

A method for detecting and measuring small quantities of amino acids utilizing the heterocyclic aromatic carbamate compounds also is the subject of the present invention. In this method, amino acids of interest are derivatized with the heterocyclic aromatic carbamate compound by reacting it with the primary or secondary amine group of the compound to form the fluorescent derivative. Derivatization of these amines results in a single product for each amino acid without the formation of interfering by-products. This simplifies quantitation of the components present.

Peptides/proteins can also be derivatized and measured using the present heterocyclic aromatic carbamate compounds. A method of detecting peptides utilizing derivatization with the present heterocyclic aromatic carbamates is also the subject of the present invention. In a typical application of the method, a protein is enzymatically or chemically digested to form peptides. The peptides are then derivatized with the carbamate compounds and analyzed to yield a peptide map, thereby providing a profile of the protein.

The heterocyclic aromatic carbamate compounds of the present invention are easy to synthesize and exhibit a higher fluorescence quantum yield than many amine-reactive derivatizing agents. Thus, in comparison to many common procedures, greater sensitivity is achieved for the detection of minute quantities of amine compounds. The derivatization process is rapid and efficient and does not involve handling of toxic or hazardous by-products. The method allows femtomole quantities of amines to be detected and measured. Some of the present heterocyclic aromatic carbamate compounds provide an additional advantage in that the emission maximum of the tagged or derivatized amine is at a significantly different wavelength than the emission maximum of the free heterocyclic amine which is used to form the activated carbamate and is a normal hydrolysis product of the derivatization reaction. Thus, the derivatized products can be distinguished from starting material and by-products.

DETAILED DESCRIPTION OF THE INVENTION

The invention relates to heterocylic aromatic carbamate reagents which are useful in forming chemical derivatives that can be employed in the analysis and purification of amines, and the synthesis of these reagents from heterocyclic aromatic amines. They are prepared in high purity (i.e., with no fluorescent impurities) via a rapid, safe and high yielding chemical reaction. The present aromatic heterocyclic carbamates have the following general formula:

wherein ArNH represents the heterocyclic aromatic amine.

The heterocyclic aromatic moiety can be any aromatic ring structure (e.g., up to about 25 carbon atoms in the ring), including polycyclic structures (e.g., up to about 5 rings), containing from about 1 to about 4 heteroatoms in the ring structure, such as nitrogen (N), oxygen (O), sulfur (S) and combinations thereof. One or multiple heteroatoms can be present outside the ring structure and include N, O, S, halogens (e.g., fluorine, chlorine and bromine) and combinations thereof. The heterocyclic moiety can be substituted with a non-reactive electron-donating group, such as alkyl (e.g., C1–C6 alkyl such as methyl or ethyl), alkoxy (e.g., C1–C6 alkoxy such as methoxy or ethoxy) or aromatic groups (e.g, phenyl). Heterocyclic aromatic amines which are useful to form the present activated carbamate compounds include, for example, aminoquinoline, substituted aminoquinoline, aminoisoquinoline, aminocoumarin, substituted aminocoumarin, aminoacridine, or a substituted aminoacridine. In addition, compounds with more than one heteroatom can take part in the formation of the carbamate compound.

The present heterocyclic aromatic carbamates are prepared by reacting the heterocyclic aromatic amine with di-(N-succinimidyl) carbonate. The reaction is shown schematically in Equation (1) below, wherein ArNH$_2$ represents the heterocyclic aromatic amine:

The reaction is generally carried out in a polar aprotic solvent, such as acetonitrile, DMF, DHSO, THF, acetone, methylene chloride, chloroform or dioxane. The solution of the amine in the solvent is added to a stirred solution of the carbonate over a period of time, preferably from about 0.5 to about 4.0 hours. After the addition is complete, the reaction mixture is stirred for a period of time (e.g., from about 1 to 24 hours) to assure complete reaction. The reaction proceeds at room temperature, however, for some reactions, improved yields can be obtained by refluxing the reaction mixture during and/or following the addition of the amine.

Novel heterocyclic aromatic carbamates of the present invention include the following compounds:

6-aminoquinolyl-N-hydroxysuccinimidyl carbamate,
3-aminoquinolyl-N-hydroxysuccinimidyl carbamate,
5-aminoquinolyl-N-hydroxysuccinimidyl carbamate,
5-aminoisoquinolyl-N-hydroxysuccinimidyl carbamate,
6-amino-4-methylquinolyl-N-hydroxysuccinimidyl carbamate,
6-amino-2,4-dimethylquinolyl-N-hydroxysuccinimidyl carbamate;
6-amino-2-phenylquinolyl-N-hydroxysuccinimidyl carbamate,
6-amino-2-methoxy-4-methylquinolyl-N-hydroxysuccinimidyl carbamate,
4-aminoquinaldine-N-hydroxysuccinimidyl carbamate,
9-aminoacridine-N-hydroxysuccinimidyl carbamate,
2-aminoacridine-N-hydroxysuccinimidyl carbamate, luminol-N-hydroxysuccinimidyl carbamate, isoluminol-N-hydroxysuccinimidyl carbamate,
7-amino-4-methylcoumarin-N-hydroxysuccinimidyl carbamate,
7-amino-4-(trifluoromethyl)coumarin-N-hydroxysuccinimidyl carbamate,
4'-(aminomethyl)fluorescein-N-hydroxysuccinimidyl carbamate,
5-(aminomethyl)fluorescesin-N-hydroxysuccinimidyl carbamate,
5-aminoeosin-N-hydroxysuccinimidyl carbamate, and
Cascade blue ethylenediamine-N-hydroxysuccinimidyl carbamate.

In one embodiment of the present method, 6-aminoquinoline was reacted with di-(N-succinimidyl) carbonate to form the corresponding carbamate, 6-aminoquinolyl-N-hydoxysuccinimidyl carbamate. The reaction is shown schematically in Equation (2).

Synthesis of this compound was carried out by reacting the amine with the carbonate in acetonitrile. A solution of the amine was added to a stirred solution of the carbonate. After the addition was complete, the reaction mixture was stirred for a period of time to assure complete reaction.

In another embodiment, the present carbamates are synthesized from heterocyclic aromatic amines via the formation of the isocyanate intermediate. This reaction requires the use of phosgene which is a hazardous and toxic material. Carbamates formed via this route may also contain impurities which fluoresce.

The present heterocyclic aromatic carbamate reagents can be used to derivatize amines in complex mixtures which allows them to be detected at the subpicomole level. The formation of the amine derivative is simple and the derivative is stable for a long enough period to allow the analyst to measure the concentration of the amines in a number of samples.

In this method, the present heterocyclic aromatic carbamate reagents are used to tag amines with a fluorescent moiety. The basic reaction used to form the derivative is shown in Equation 3. The carbamate reacts quickly with the amine to form the derivative.

(3)

In this equation, R'NH$_2$ represents the amine compound of interest.

The present compounds have a heterocyclic aromatic group which exhibits a higher fluorescence quantum yield than that of carbocyclic aromatics used as tags in other derivatizing reactions. Nimura et al., *Anal. Chem.*, 58:2372 (1986). This increase in the fluorescence quantum yield of the tag provides an increase in the sensitivity of the tagged amine. The present method provides a process for producing these heterocyclic aromatic carbamates, which have not previously been available.

For some of the present heterocyclic aromatic carbamates, the emission maximum of an amine compound derivatized with the carbamate is at significantly different wavelength than the emission maximum of the free heterocyclic amine which is used to form the carbamate. For example, free 6-aminoquinoline has an emission maximum at 550 nm; however, when the fluorescent moiety is bound to a protein, the emission maximum is at 375 nm. Brynes, Bevilaqua and Green, *Anal. Biochem.*, 116:408 (1981).

This wavelength shift has very significant implications for fluorescence detection of tagged amines. To detect the tagged amines, using the 6-aminoquinoline derivative, for example, the emission monochromator is set at 395 nm, for example, where the 6-aminoquinoline derivatized amines fluoresce. At that wavelength, the fluorescence from the free 6-aminoquinoline will be negligible. Since the observed fluorescence is predominantly from the derivative, background noise is eliminated or reduced and a more sensitive assay is obtained.

In contrast, for most tagging derivatizing agents, the emission characteristics of the tagged amine, any unreacted derivatizing agent, and hydrolysis products of the derivatizing agent are very similar. This can create a very significant analytical problem, since it is necessary to ensure that any unreacted derivatizing agent and/or the product(s) from the hydrolysis of the derivatizing agent which may fluoresce do not interfere with the detection of the tagged amines. In the present method of derivatizing amines, any unreacted carbamate reagent will be hydrolyzed to the free amine under the conditions of the derivative-forming reaction. Thus, if 6-aminoquinoline is used to form the heterocyclic aromatic carbamate, for example, its presence does not interfere with the assay of tagged amines.

The analysis of amines by this technique provides a significant improvement in the minimum detectable limit of amines. In typical experiments using the present heterocyclic aromatic carbamates, the minimum detectable limit for amines is improved by at least an order of magnitude; thus a limit of 100 femtomole (fmol = $10^{-15}$ moles) of many amines can be detected by using a carbamate formed from 6-aminoquinoline or other heterocyclic aromatic amines. When the carbamate reagent is formed from a non-heterocyclic amine, namely naphthylamine, the detection limit was 0.15–0.3 ng (1–2 pmol; pmol = $10^{-12}$ moles). Nimura, et al., ibid. Thus, the use of a heterocyclic aromatic moiety as the tag provides at least an additional order of magnitude of sensitivity. Therefore, an order of magnitude less sample is required for analysis.

Derivatized amines formed using the present carbamate reagents are formed within minutes, and are stable in solution for a period of at least 14 days. The reagents allow amines in complex samples to be detected and measured at the 100 femtomole level.

The present compositions and methods are particularly useful for derivatizing and detecting amino acids. The basic reaction used to form the derivative is shown in equation (4). In this equation, Ar is the heterocyclic moiety and R' represents the side chain of the amino acid.

(4)

The following heterocyclic aromatic carbamate reagents are preferred for this purpose:

6-aminoquinolyl-N-hydroxysuccinimidyl carbamate,
3-aminoquinolyl-N-hydroxysuccinimidyl carbamate,
5-aminoquinolyl-N-hydroxysuccinimidylcarbamate,
5-aminoisoquinolyl-N-hydroxysuccinimidyl carbamate,
6-amino-4-methylquinolyl-N-hydroxysuccinimidyl carbamate,
6-amino-2,4-dimethylisoquinolyl-N-hydroxysuccinimidyl carbamate,
6-amino-2-phenylquinolyl-N-hydroxysuccinimidyl carbamate,
6-amino-2-methoxy-4-methylquinolyl-N-hydroxysuccinimidyl carbamate,
4-aminoquinaldine-N-hydroxysuccinimidyl carbamate, and
9-aminoacridine-N-hydroxysuccinimidyl carbamate.

The general methodology for the analysis of amino acids consists of three closely related processes: (1) formation of derivatives of the amino acids in the sample; (2) separation of the amino acid derivatives; and (3) detection of the separated derivatives. The first step is generally performed by reacting a mixture containing the amino acids with one of the present carbamate reagents to yield a distinct compound for each amino acid. These derivatives provide a fluorescent signal which can then be detected in the detection stage of the analysis. The present heterocyclic compounds are particularly useful for derivatizing amino acids because they react quickly with the amino acid and form a stable, highly fluorescent derivative.

The separation step is based upon the differences in the chemical structure of the derivatives. The derivatized amino acids differ from each other in the same way that the chemical structures of the precursor amino acids differ. The derivatives must be separated so that the detector signal can be correctly related to the concentration of each derivative. The derivatized amino acids can be separated and detected by chromatography, e.g., by high performance liquid chromatography (HPLC) or capillary zone electrophoresis (CZE). HPLC is particularly useful for this purpose. These technologies are well suited for this purpose because they are selective and can be used with very small samples. It is also possible to carry out the separation step by separating the amino acids prior to their derivatization.

The detection step is generally carried out using either an absorbance or fluorescence detector. As each derivative is eluted from the chromatographic column after step (2), its presence and quantity is detected by the absorbance or emission of light. The sensitivity of the assay depends upon the strength of the signal from each amino acid. The present carbamate compounds exhibit a high quantum absorbance, thereby allowing detection of femtomole quantities.

Figure 1A:
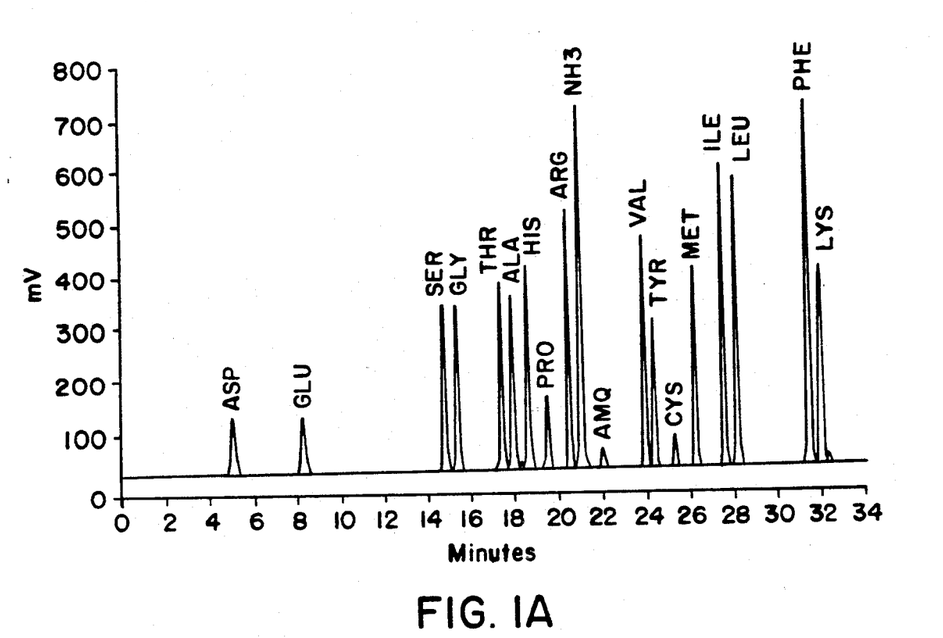
FIG. 1A shows a chromatogram of amino acid derivatives using 6-aminoquinolyl-N-hydroxysuccinimidylcarbamate as the tagging agent (fluorescence detection, excitation 245 nm, emission 395 nm). The separation was performed on a NovaPak TM Phenyl column (Waters, Division of Millipore).
Figure 1B:
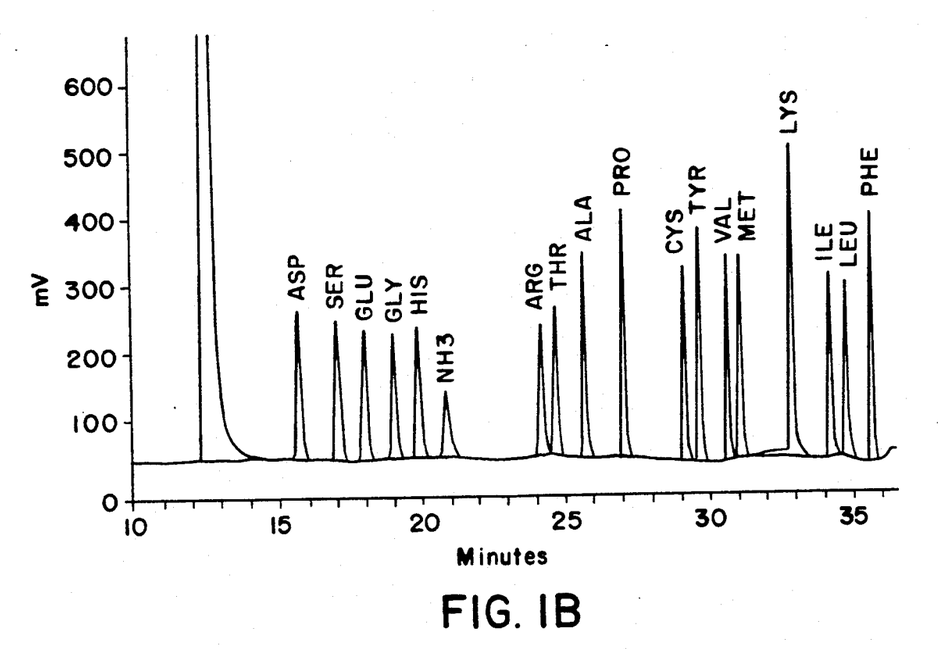
FIG. 1B shows the same separation as performed in FIG. 1A (detection by UV at 254 nm) except using a NovaPak TM C18 column (Waters, Division of Millipore).
Figure 2A:
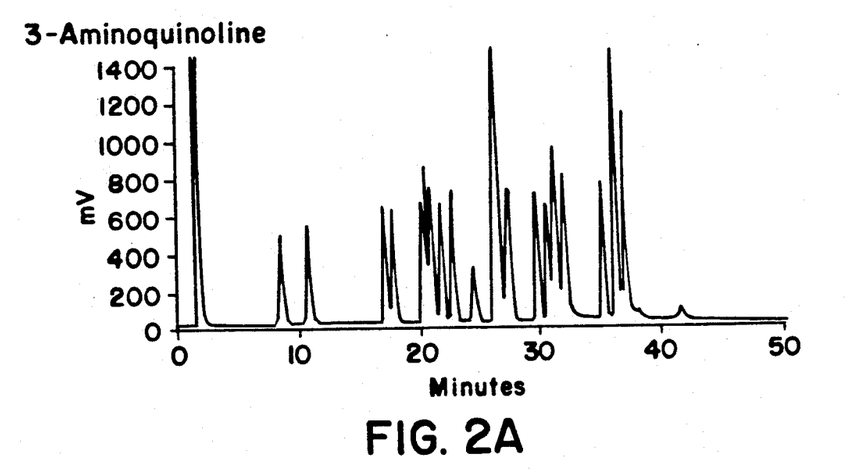
FIG. 2 shows the results of an HPLC separation of amino acid derivatives using (A) 3-aminoquinoline, (B) 9-amino-acridine and (C) 7-amino-4-methylcoumarin.
Figure 2B:
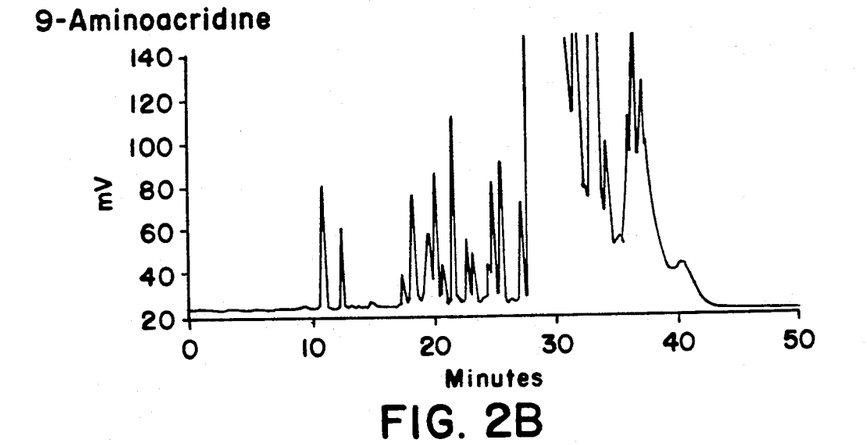
Figure 2C:
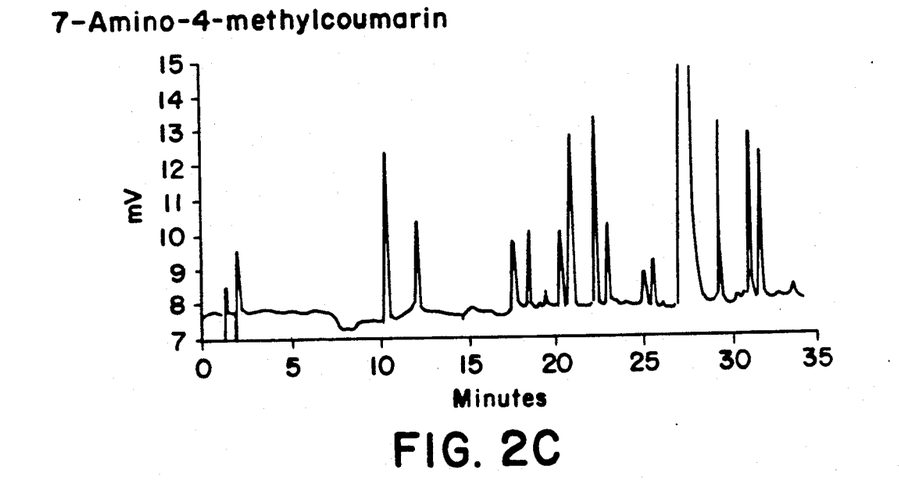

A typical HPLC separation of the derivatives using 6-aminoquinoline is shown in FIG. 1. The separation of other representative derivatives using 3-aminoquinoline, 9-amino-acridine and 7-amino-4-methylcoumarin, are shown in FIG. 2.

In another embodiment of the present method, the heterocyclic aromatic carbamate reagents are used to tag peptides with a fluorescent moiety. The basic reaction is the same as that used to form amino acid derivatives, shown in Equation (4) above. The carbamate reacts quickly with the peptide to form the derivative. When the reagent reacts with a peptide, the heterocyclic aromatic moiety will become a part of the compound which is ultimately detected, as described above.

The analysis of peptides and/or proteins by this technique provides a significant improvement in the minimum detectable limit of peptides. In typical experiments, the minimum detectable limit for peptides is improved by an order of magnitude; thus a limit of 100 fmol can be detected by using a carbamate reagent formed from the present heterocyclic aromatic amines.

The present heterocyclic aromatic carbamates are useful in peptide/protein mapping. Peptide mapping is a powerful technique used in the characterization of the structure of a protein. In this method, a protein is enzymatically or chemically digested to form peptides, which are shorter chains of the amino acids. The cleavage products contain the amino acids in precisely the same sequence as in the original protein. The benefit of cleaving the protein is to provide the analyst with smaller segments which are easier to study. A variety of enzymes and reagents can be used to cleave a protein; each will provide a different collection of peptides. These digests are then analyzed to yield a "peptide map", which is a unique profile of the protein. The peptide mapping data is compared to reference chromatograms to establish the equivalency of the protein of interest, or to assist in the determination of the structure of an unknown protein, e.g. to determine mutational variants.

Reverse phase HPLC is generally used to analyze the peptide digests. In a given peptide digest there may be from 20 to 150 different peptides, each of which must be resolved and quantitated. In many instances, the available sample is very small. For example, the analyst may be determining the structure of a protein that is isolated from an organism or one that has been synthesized by recombinant DNA technologies. Typically, nanomole quantities of a protein digest are studied. Due to the scarcity and cost of many proteins, it is very desirable to use as small a sample as possible.

Absorbance detection is generally used in protein mapping work. Two different detection processes which are often used for this purpose are: a) detection at 210–215 nm using a single wavelength detector; and b) broadband spectral detection using a photodiode array (PDA) detector. In the first method, all peptides absorb at that wavelength, thus the user can ensure that all peptides eluted from the column are detected. One difficulty with this technique is that a wide variety of compounds absorb in this region of the spectrum, and extreme care must be taken to ensure that all reagents, eluants, glassware, etc. are scrupulously clean to ensure that the observed signal is solely from the peptides. In the second method, the PDA detector collects the spectra of the eluent at specific time intervals (e.g. a spectrum between 200 and 350 nm is collected every second). This provides more information than a single wavelength and thus can assist in distinguishing between peptides which may elute with similar retention times.

Peptide mapping often involves the qualitative and quantitative analysis of trace levels of peptides in the digested protein. The identification and quantitation of peptides in complex mixtures in the present method is effected by a three stage process: a) tagging the peptides of interest with the heterocyclic aromatic carbamates, which exhibit a stronger absorbance or fluorescence signal than the original compound; b) separating the derivatized samples; and c) detecting the derivatized peptides by absorbance or fluorescence techniques. The separation conditions for a derivative are frequently drastically different from the separation of the starting compounds. Likewise, the efficiency of a separation has a serious impact on the detection process. Use of the present heterocyclic aromatic carbamates provides a mapping method adaptable for use with nanogram quantities of protein. Further, the methods of this invention provide a means for enhancing the sensitivity of known methodologies for detecting peptides in biological samples, such as tissue, urine, blood and saliva.

The invention will now be further illustrated by the following examples.

EXAMPLES

Example 1

Synthesis of 6-Aminoquinolyl-N-hydroxysuccinimidyl carbamate

6-Aminoquinolyl-N-hydroxysuccinimidyl carbamate was synthesized according to the following procedure. Acetonitrile (500 ml, Baker analyzed HPLC grade) was distilled to azeotropically remove any water present. The first 50 ml of acetonitrile was discarded. 6-Aminoquinoline (1.5 g, 10 mmol, Aldrich Chemical Co.) was dissolved in 50 ml of acetonitrile and placed in an addition funnel. Di(N-succinimidyl) carbonate (DSC; 3 g., 12 mmol, Fluka Chemical Co.) was dissolved in 100 ml. of acetonitrile and heated to reflux with stirring. The aminoquinolino solution was added dropwise to the refluxing solution over a period of about 30 minutes.

After the addition was complete, the solution was refluxed for another 30 minutes, and then about 30 ml of acetonitrile were distilled from the reaction mixture. The solution was allowed to cool and was seeded with aminoquinolyl-N-hydroxysuccinimidyl carbamate. After 24 hours, the solution was decanted and the crystals were filtered and washed with 100 ml of acetonitrile in portions to yield 1.95 g (66% of crude product. The mother liquor contained additional product along with DSC, N-hydroxy-succinimide and 1,3-di(6-aminoquinolyl) urea. The product was recrystallized by dissolving the crude material in hot acetonitrile (100 ml/g product), filtering the solution through a 0.5 μm filter and seeding the filtrate with 6-amino-quinolyl-N-hydroxysuccinimidyl carbamate. A 24% overall yield of (724 mg) of product was obtained.

Example 2

Synthesis of-3-Amino-quinolyl-N-hydroxysuccinimidyl carbamate

3-Aminoquinolyl-N-hydroxysuccinimidyl carbamate was synthesized according to the procedure described in Example 1, except that 3-aminoquinoline was used in lieu of 6-aminoquinoline, the amine solution was added to the carbonate solution over three hours and the reaction was performed at room temperature. After addition of the amine was complete, 20% of the acetonitrile was removed by rotary evaporation. The resulting concentrated solution was then frozen to cause precipitation of the solid product.

Example 3

Synthesis of 9-Aminoacridine-N-hydroxysuccinimidyl carbamate

9-Aminoacridine-N-hydroxysuccinimidyl carbamate was synthesized according to the procedure described in Example 1, except that 9-aminoacridine was used in lieu of 6-aminoquinoline. The reaction was performed at reflux temperature. The amine solution was added to carbonate solution over a two hour period. After addition of the amine was complete, 80% of the acetonitrile was removed by rotary evaporation. The resulting concentrated solution was placed in the freezer and the solid product precipitated.

Example 4

Synthesis of 7-Amino-4-methylcoumarin-N-hydroxysuccinimidyl carbamate

7-Amino-4-methylcoumarin-N-hydroxysuccinimidyl carbamate was synthesized according to the procedure described in Example 1, except that 7-amino-4-methylcoumarin was used in lieu of 6-aminoquinoline. The reaction was performed at room temperature with stirring. The amine solution was added over a period of four hours. Fractional recrystallization of the product was performed using acetonitrile to purify the carbamate product.

Example 5

General Procedure for Derivatization of Amines with a Heterocyclic Aromatic Carbamate Standard calibration solutions are prepared by the following procedure: 5 μl of standard solution of amine (0.1 nmole/μl) was prepared, and 35 μl of borate buffer (0.2M borate, 5 MM EDTA) was added. To this mixture was added 10 μl of the reagent solution (3 mg carbamate compound in 1 ml HPLC-grade acetonitrile). The resulting mixture was heated to 70° C. for 5 minutes.

Derivatives were prepared by adding 10 μl of 10 MM HCl to deproteinized sample and vortexing. Borate buffer (30 μl) was added to this mixture, then 10 μl of the carbamate reagent solution was added. The resulting mixture was heated to 70° C. for 5 minutes.

The reaction is very rapid and derivatized products are formed virtually immediately. The solution, however, is then heated to 50°-70° C. to quantitatively convert tyrosine into a single, stable derivative. At ambient conditions, tyrosine also yields a second derivative which slowly converts to the stable form.

Example 6

The HPLC separation of amino acid derivatives prepared as described in Example 5 was effected using a reverse phase column. A gradient elution procedure using a buffer system with an organic modifier was employed. The following conditions were used to separate a standard protein hydrolysate mixture containing 17 amino acids and ammonia using 6-aminoquinolyl-N-hydroxysuccinimidyl-carbamate as the tagging agent.

a) Column: A column packed with NovaPak TM Phenyl (Waters, Division of Millipore) (15 cm × 3.9 mm column) was used for the amino acid hydrolysates. Waters HPLC System including 2 M510 pumps, M712 autosampler, M440 absorbance detector, M470 fluorescence detector, column temperature control module and M860 data system.

b) Mobile Phases: Mobile phase (A): 60 mM Sodium Acetate, (pH 6.35). Mobile phase (B): 60% acetonitrile. Gradient: 0–20% Mobile phase B using a linear gradient over a period of 30 minutes.

c) Temperature: 35° C.

5 μl of a standard, prepared as described in Example 5, was first injected followed by injection of 10 μl of sample. Fluorescence detection of the amino acid derivatives formed from the activated carbamate was effected by excitation at 245 nm, emission at 395 nm. The results are shown in FIG. 1A.

The same separation was carried out using a Nova-Pak C18 column (3.9 mm × 15 cm). Mobile phase A was 140 mm sodium acetate, 17 mm triethylamine, pH 4.95. Detection was performed with U.V. at 254 nm. The results of this separation are shown in FIG. 1B.

Example 7

Capillary electrophoresis was also be used to separate and detect amino acid derivatives made by the present method. The capillary electrophoresis separation of the derivatives was effected using the following conditions using a Waters Quanta 4000 Capillary Electrophoresis System with 254 nm detection.

Separation Solution: 0.05M pH=9.5 aqueous sodium borate buffer with methanol (90:10) and 0.05M sodium dodecylsulfate. Capillary tube: 60 cm long, 50 micron (I.D.) fused silica with a polyimide coating. Voltage=20 KV

Figure 3:
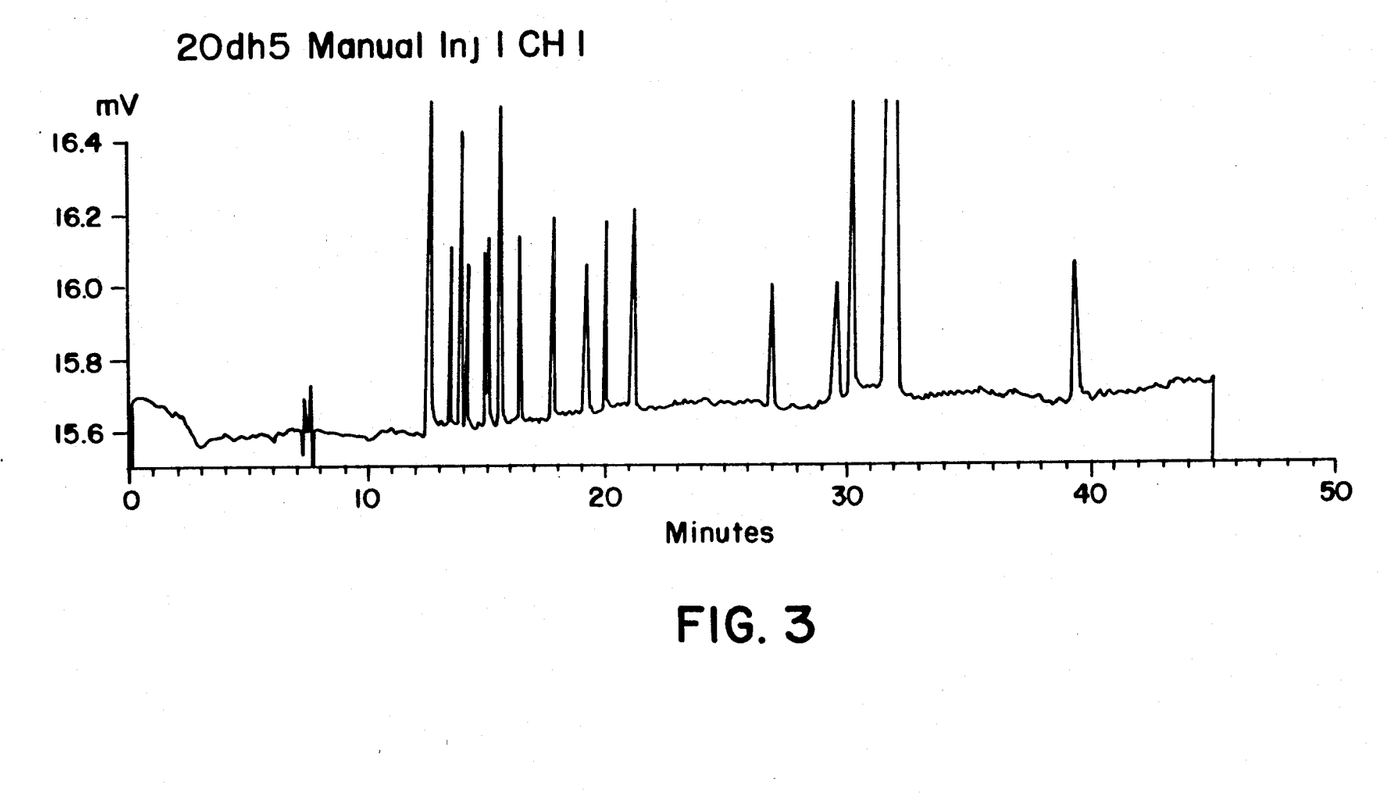
FIG. 3 shows a chromatogram from a capillary electrophoresis separation of amino acid derivatives. 10 fold diluted hydrolysate (250 μMol/l).

Absorbance detection was used at 254 nm. Results are shown in FIG. 3.

Equivalents

Those skilled in the art will recognize, or be able to ascertain, using no more than routine experimentation, many equivalents to the specific embodiments of the invention described herein. An example of such an equivalent would be the detection of derivatized components by means other than fluorescence, including chemiluminescence or electrochemical response. Such equivalents are intended to be encompassed by the following claims:

We claim:

1. A heterocyclic activated carbamate compound having the formula:

wherein Ar is quinolyl, acridinyl, coumarin or fluorescein which may be substituted with alkyl, alkoxy, OH, halo, amino, sulfur, oxygen or phenyl.

2. A heterocyclic aromatic carbamate compound selected from the group consisting of:

a) 6-aminoquinolyl-N-hydroxysuccinimidyl carbamate,
b) 3-aminoquinolyl-N-hydroxysuccinimidyl carbamate,
c) 5-aminoquinolyl-N-hydroxysuccinimidyl carbamate,
d) 5-aminoisoquinolyl-N-hydroxysuccinimidyl carbamate,
e) 6-amino-4-methylquinolyl-N-hydroxysuccinimidyl carbamate,
f) 6-amino-2,4-dimethylquinolyl-N-hydroxysuccinimidylcarbamate,
g) 6-amino-2-phenylquinolyl-N-hydroxysuccinimidylcarbamate,
h) 6-amino-2-methoxy-4-methylquinolyl-N-hydroxysuccinimidylcarbamate, and
i) 4-aminoquinaldine-N-hydroxysuccinimidyl carbamate.

3. Aminoquinolyl-N-hydroxysuccinimidyl carbamate.

4. A heterocyclic aromatic carbamate compound selected from the group consisting of:

a) 9-aminoacridine-N-hydroxysuccinimidyl carbamate,
b) 2-aminoacridine-N-hydroxysuccinimidylcarbamate,
c) luminol-N-hydroxysuccinimidylcarbamate,
d) isoluminol-N-hydroxysuccinimidylcarbamate,
e) 7-amino-4-methylcoumarin-N-hydroxysuccinimidylcarbamate,
f) 7-amino-4-(trifluoromethyl)coumarin-N-hydroxysuccinimidylcarbamate,
g) 4'-(aminomethyl)fluorescein-N-hydroxysuccinimidylcarbamate,
h) 5-(aminomethyl)fluorescein-N-hydroxysuccinimidylcarbamate,
i) 5-aminoeosin-N-hydroxysuccinimidylcarbamate; and
j) Cascade Blue ethylenediamine-N-hydroxysuccinimidylcarbamate.

* * * * *